(12) United States Patent
Carden et al.

(10) Patent No.: US 9,597,265 B2
(45) Date of Patent: Mar. 21, 2017

(54) METHOD AND APPARATUS FOR PREPARING A CERAMIC DENTAL RESTORATION IN ONE APPOINTMENT

(71) Applicant: James R. Glidewell Dental Ceramics, Inc., Newport Beach, CA (US)

(72) Inventors: Robin A. Carden, San Juan Capistrano, CA (US); Michael J. Selberis, Ladera Ranch, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 534 days.

(21) Appl. No.: 13/900,805

(22) Filed: May 23, 2013

(65) Prior Publication Data

US 2013/0316305 A1 Nov. 28, 2013

Related U.S. Application Data

(63) Continuation-in-part of application No. 13/481,811, filed on May 26, 2012, now abandoned.

(51) Int. Cl.
*A61C 13/00* (2006.01)
*A61K 6/00* (2006.01)
*A61K 6/02* (2006.01)

(52) U.S. Cl.
CPC .......... *A61K 6/024* (2013.01); *A61C 13/0022* (2013.01); *A61K 6/0088* (2013.01)

(58) Field of Classification Search
None
See application file for complete search history.

(56) References Cited

U.S. PATENT DOCUMENTS

| 6,455,451 B1 | 9/2002 | Brodkin et al. |
| 6,663,387 B2 | 12/2003 | Riley |
| 8,178,012 B1 | 5/2012 | Khan et al. |

(Continued)

FOREIGN PATENT DOCUMENTS

| WO | WO0135854 | 5/2001 | |
| WO | WO 2012087997 A1 * | 6/2012 | ......... A61C 13/0022 |

OTHER PUBLICATIONS

International Search Report in International Application No. PCT/US2013/042410 mailed Oct. 31, 2013.

(Continued)

*Primary Examiner* — David Sample
*Assistant Examiner* — Nicholas W Jordan
(74) *Attorney, Agent, or Firm* — Dianne Burkhard; Charles Fowler

(57) ABSTRACT

Methods and apparatus that permit a dentist to provide a patient with a monolithic ceramic dental restoration (e.g., crown, bridge, or the like) in one office visit. In some embodiments, a dentist is provided with a kit containing one or more near net shape (NNS) millable blanks of various shapes and shades, chair-side software, and a chair-side milling machine to convert a selected millable blank into a finished, fully contoured restoration in about one hour or less. Each such millable blank may be, for example, a dental ceramic (e.g., fully sintered zirconia, fully crystallized lithium silicate, fully crystallized lithium disilicate, or the like) NNS component. In some embodiments, the NNS component includes an integral mandrel at a precise location and orientation to minimize the amount of milling time.

20 Claims, 8 Drawing Sheets

(56) References Cited

U.S. PATENT DOCUMENTS

| | | |
|---|---|---|
| 2005/0008887 A1 | 1/2005 | Haymann et al. |
| 2005/0276672 A1 | 12/2005 | Prince |
| 2006/0172263 A1 | 8/2006 | Quadling et al. |
| 2010/0233655 A1 | 9/2010 | Karim et al. |
| 2011/0065066 A1* | 3/2011 | Segawa .................. B24B 55/02 433/201.1 |
| 2011/0287382 A1 | 11/2011 | Johnson et al. |
| 2012/0088208 A1 | 4/2012 | Schulter et al. |
| 2012/0139141 A1* | 6/2012 | Khan .................. A61C 13/082 264/20 |
| 2012/0282572 A1 | 11/2012 | MacLeod et al. |

OTHER PUBLICATIONS

U.S.P.T.O. Non-Final Office Action issued in U.S. Appl. No. 13/481,811 dated May 8, 2014.
U.S.P.T.O Non-Final Office Action issued in U.S. Appl. No. 13/481,811 dated Oct. 16, 2013.

* cited by examiner

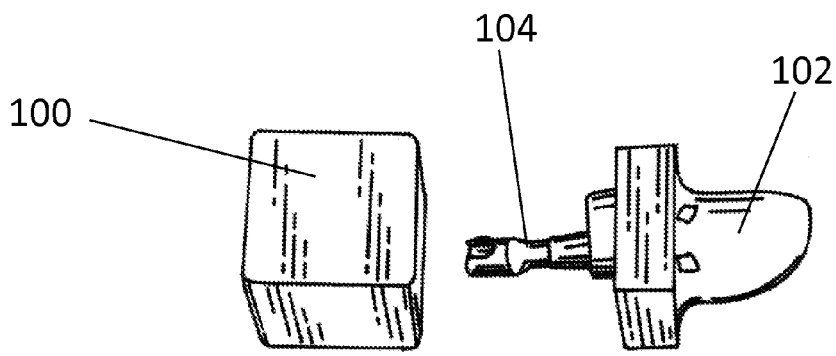
FIG. 1A
PRIOR ART
FIG. 1B
PRIOR ART
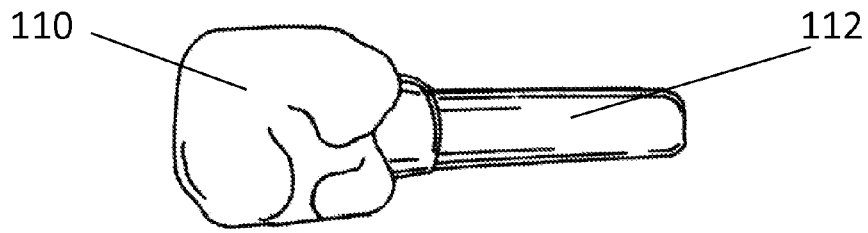
FIG. 1C
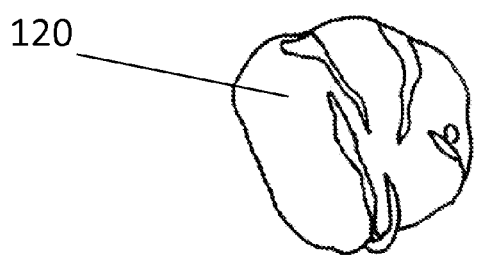
FIG. 1D
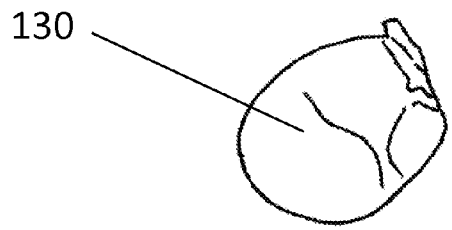
FIG. 1E

METHOD AND APPARATUS FOR PREPARING A CERAMIC DENTAL RESTORATION IN ONE APPOINTMENT

RELATED APPLICATION

This application is a continuation-in-part of U.S. patent application Ser. No. 13/481,811, filed on May 26, 2012, which application is incorporated by reference herein in its entirety.

FIELD

The methods and apparatus described herein relate generally to the field of restorative dentistry. The methods and apparatus relate more specifically to the extremely rapid fabrication of ceramic (e.g., zirconia, lithium silicate, lithium disilicate) dental restorations to permit preparation of, for example, zirconia, lithium silicate, or lithium disilicate crowns, bridges, or other restorations in a dental office during a single visit by a patient.

BACKGROUND DISCUSSION

There are several important advantages to ceramic dental restorations, including zirconia, lithium silicate, and lithium disilicate dental restorations that make them ideal material for use as dental crowns, bridges and the like. First, they are very strong and therefore highly resistant to chipping, breakage and wear. For example, the assignee hereof has achieved a flexure strength exceeding 1600 MPa in monolithic zirconia crowns. Second, they can be shaped, sized and colored to take on a natural appearance that is essentially undistinguishable from the original teeth they restore or replace. Third, they can be fabricated in a manner which results in a cost effective restoration when compared to conventional materials such as PFM.

There is yet another potential fourth advantage which has not been fully realized in the dental restoration art. This advantage would, if achievable, result from the qualities of a monolithic ceramic material, including zirconia, lithium silicate, and lithium disilicate, which can be fabricated in distinct steps that need not be accomplished all at one time. This advantage would be realized at the dentist's office where it would significantly reduce the time required to fully fabricate a patient/tooth specific finished restoration within a time period so short that it can be conveniently accomplished while the patient is in the dental office and even while in the dental chair. Such time periods to be practical would have to be one hour or less, including the time a patient first sits in a dental chair to be examined for a new crown and until that same patient exits the dental chair with a newly installed crown. And not just any standard crown, but, in some embodiments, one that is stronger, equal to, or better than the natural tooth in appearance and reasonably priced, or even less costly than conventional crowns. Such an invention could realistically change a significant part of the dental profession and the dental laboratory industry.

SUMMARY

In several embodiments, the methods and apparatus described herein provide users with the ability to achieve the fourth advantage alluded to above. In some embodiments, the first step of a method for preparing a ceramic dental restoration is to fabricate a near net shape (NNS), fully sintered, monolithic ceramic (e.g., zirconia, lithium silicate, lithium disilicate) millable blank of selected shading. In some embodiments, the NNS millable blank includes an integral ceramic (e.g., zirconia, lithium silicate, or lithium disilicate) mandrel. The mandrel extends from a selected location on the NNS millable blank and at a precisely known angle. In several embodiments, the second and subsequent steps of the described method comprise fabricating other NNS ceramic millable blanks of selected shading and having an integral ceramic mandrel, until a plurality of such NNS millable blanks may be assembled to form a kit having a plurality of likely general shapes and shadings of ceramic material that may be needed for the vast majority of patients a dentist is likely to see in the course of his or her practice. It will be seen hereinafter that for single tooth crowns, in some embodiments, there are up to seventy or more variations of combined shape and shading in an exemplary kit. In some embodiments, such a kit would be kept in a dentist's office along with a chair-side milling machine to be described hereinafter.

The next step in the method of another embodiment is to perform an optical scan of the patient's mouth adjacent the tooth to be restored. An impression can also be used to generate the scanning file. This scan generates data which is sent to a computer with designing software which could be located at the doctor's office or in the cloud via an internet connection. The dental office, the lab, or the automated process in the cloud hereof then generates a corresponding file to control the aforementioned milling machine and indicates an appropriate NNS millable blank to be used from the kit. The appropriate digital milling strategy is calculated either by the software located in the doctor's office, dental lab or via the cloud service and is sent electronically to the dentist's office milling machine to control the machine's conversion of the selected NNS millable blank to a finished restoration which may need only slight polishing, or glazing to complete after (in some embodiments) the integral mandrel is separated from the milled restoration's surface.

One aspect of the method hereof is the time required to convert the NNS millable blank to a finished restoration. For example, current zirconia milling strategies involve milling a porous zirconia body and then sintering at high temperatures, 1300-1600 C, which takes many hours to complete. A porous "block body shape" is used because of the time it takes to mill a fully dense restoration which is usually many hours and expensive because of the many diamond burrs. Similarly, many current lithium silicate and lithium disilicate millable blocks are machined in a pre-crystalized or partially crystallized state, then fully crystallized in a separate heating process. Because the millable blanks described herein are near net shape, the amount of ceramic material to be removed by the chair-side milling machine is significantly reduced. In some embodiments, the integral mandrel further reduces the amount of ceramic material that needs to be removed because there is no significant angular error or imprecision between the mandrel and the restoration. Because the total amount of material to be removed may be as little as a few grams, the time required using the chair-side milling machine to convert the millable blank to a finished restoration is typically less than ten minutes. In some embodiments, the apparatus hereof comprises a kit and a chair-side milling machine at a dentist's office and the dental office, laboratory or cloud-located software for converting a patient's mouth scan data into a millable blank selection and milling machine instructions to mill the restoration.

In order to minimize the amount of excess material that will need to be removed in the chair-side milling machine and still require a kit having only a reasonable number of near net shape millable blanks, in some embodiments the shape and size of an NNS millable blank is derived from a large database of possible tooth shapes and sizes. In one embodiment, each such NNS component is derived from a composite of literally thousands of actual teeth of each type, i.e., upper molar, lower molar, incisors, etc. That composite is then smoothed by filling between peaks to provide an NNS millable blank that is easy to manufacture by an efficient process such as by injection molding and then fully sintered and placed into the kit with one of various alternative shading colors to provide a starting work piece for the chair-side milling step. A suitable chair-side milling machine is disclosed in co-pending U.S. patent application Ser. No. 13/495,620 filed on Jun. 13, 2012, which is hereby incorporated by reference in its entirety.

BRIEF DESCRIPTION OF THE DRAWINGS

The aforementioned objects and advantages of the present methods and apparatus, as well as additional objects and advantages thereof, will be more fully understood herein after as a result of a detailed description of several embodiments when taken in conjunction with the following drawings in which:

FIGS. 1A and 1B are perspective views showing a prior art millable block and a prior art partially milled restoration, respectively;

FIG. 1C is a perspective view of a near net shape (NNS) ceramic millable blank that includes an integral ceramic mandrel;

FIG. 1D is a perspective view of a restoration milled from an NNS ceramic millable blank;

FIG. 1E is a perspective view of a near net shape (NNS) ceramic millable blank that is not attached to a mandrel;

DETAILED DESCRIPTION

Figure 2:
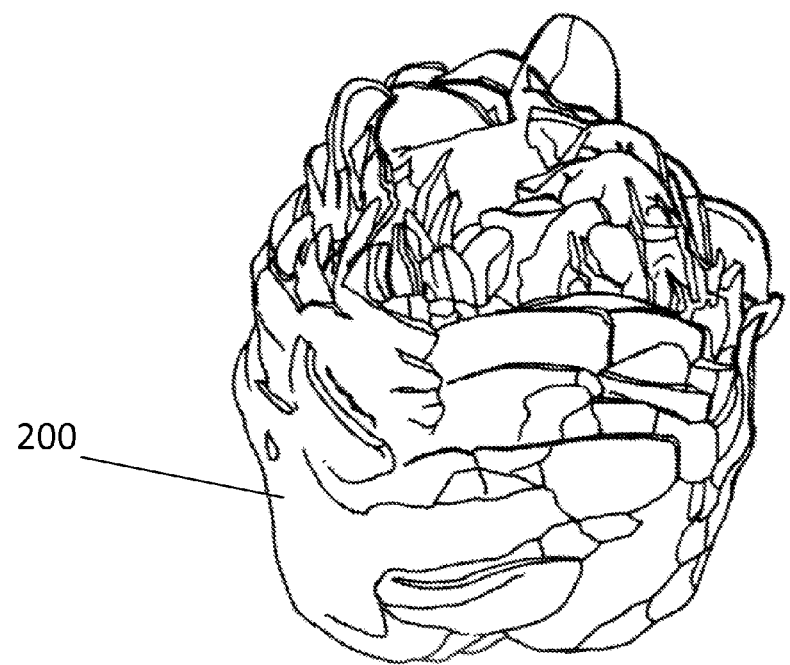
FIGS. 2 through 5 are drawings of a crude shape molar corresponding to a step in the creation of an NNS millable blank according to one embodiment of the invention.
Figure 3:
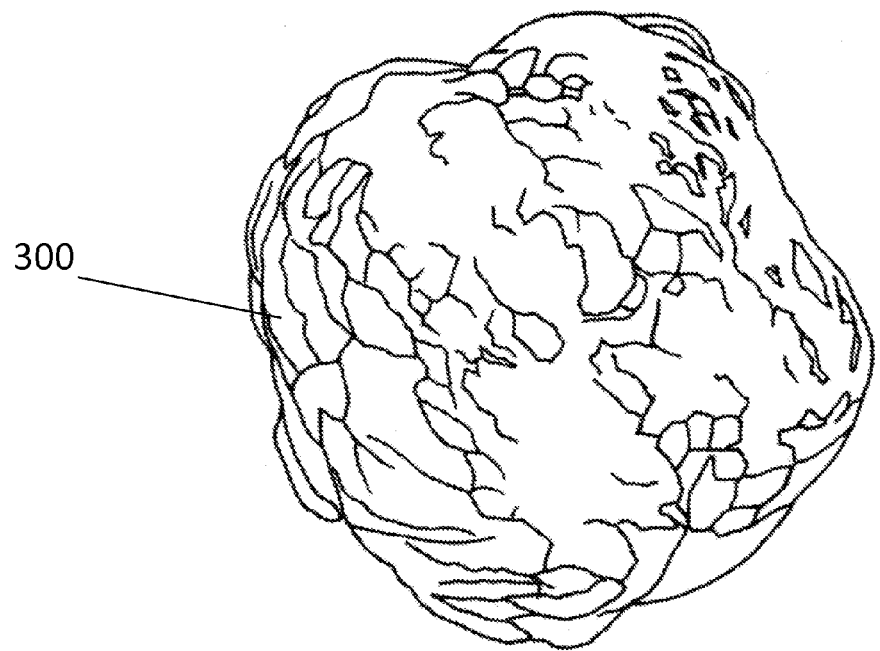
Figure 4:
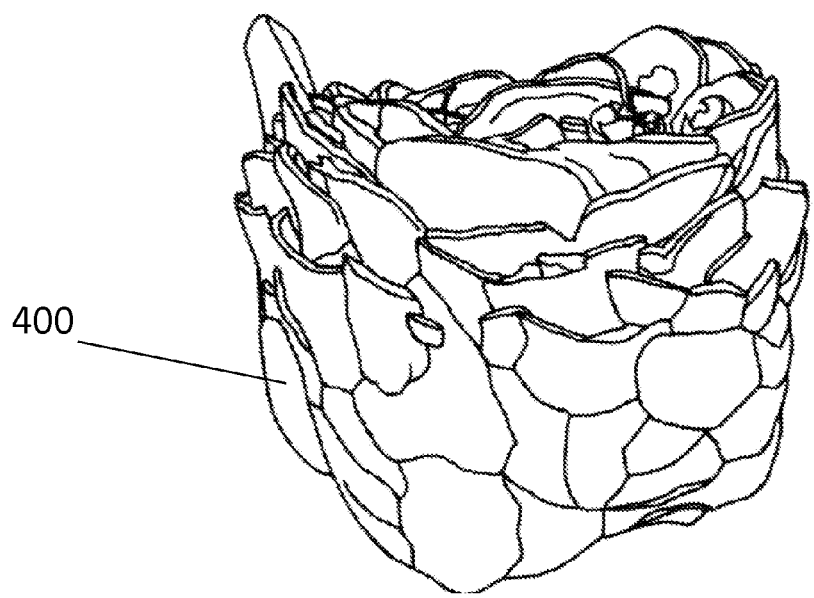
Figure 5:
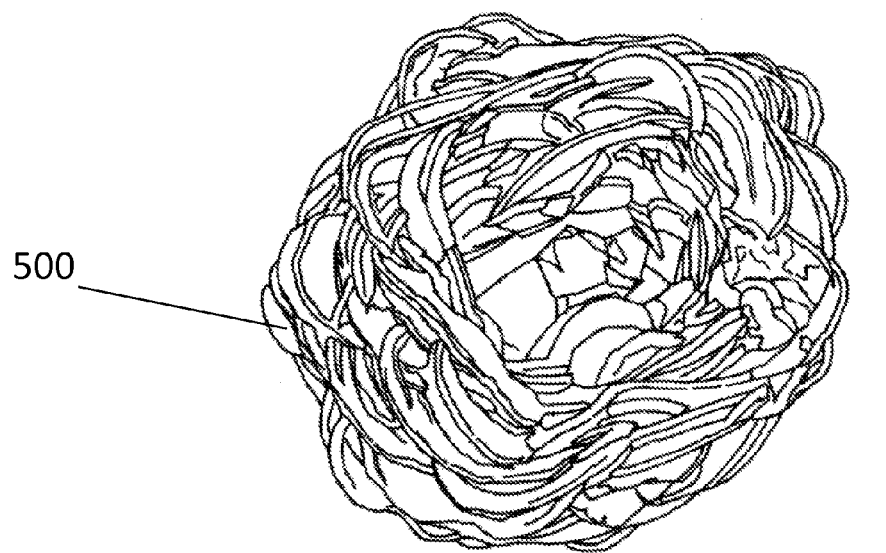

The methods and apparatus described herein are suitable for use with ceramic materials used in dental restorations. As used herein, unless the context dictates otherwise, the term "ceramic materials" shall refer to conventional ceramic materials (e.g., zirconia (zirconium dioxide) and others) as well as glass-ceramic materials (e.g., lithium silicate, lithium disilicate, alumino-silicate, rare earth metal oxide silicates, other metal oxide silicates, and others) used in the dental restoration art. Examples of zirconia ceramic materials are described, for example, in U.S. Pat. No. 8,298,329; U.S. Patent Application Publication No. 2009/0115084; and U.S. patent application Ser. No. 13/659,209, filed Oct. 24, 2012. Examples of lithium silicate glass-ceramic materials are described, for example, in U.S. Pat. No. 7,892,995; U.S. Patent Application Publication No. 2012/0094822; and U.S. patent application Ser. No. 13/685,450, filed Nov. 26, 2012. Examples of lithium disilicate glass-ceramic materials are described, for example, in U.S. Pat. Nos. 6,802,894, 7,452,836, 7,816,291, and 8,444,756. Each of the foregoing patents, publications, and applications is hereby incorporated by reference herein in its entirety.

Referring to the accompanying drawings, it will be seen that the methods and apparatus described herein provide a reduction in the time required to prepare a finished ceramic restoration. For example, one of the reasons why zirconia, lithium silicate, and lithium disilicate have become such desirable materials for use in restorative dentistry is the strength and durability of these ceramic materials. However, this feature also makes it more difficult to machine such as by milling after the material has been fully sintered or crystallized. Milling any significant amount of material from a fully sintered zirconia block, can be a time-consuming process that would ordinarily make it impractical to provide a finished zirconia restoration within one patient visit. The conventional approach has been to shape the zirconia while it is only partially sintered and therefore more readily milled. However, such a two-step approach makes it impractical to complete a finished fully formed zirconia restoration during one patient visit without having a sintering oven on the premises. While the assignee hereof has designed such an oven that is capable of high speed sintering at a dental office, there may be some reluctance among dentists to have to deal with a high temperature, high power apparatus at their facility and to calculate sintering induced shrinkage resulting from full sintering. Similarly, it is known to use a two-step process for machining a block of partially crystallized lithium silicate or lithium disilicate material, followed by heat-treating the machined component to obtain a fully crystallized final restoration. Therefore, the present invention is designed to make it practical for dentists to work with fully sintered and fully crystallized components, which because of their unique near net shape configuration and (in some embodiments) integral mandrel, make it possible to mechanically finish the restoration in a relatively brief period of time. In some embodiments, the dentist is provided with fully sintered or fully crystallized, near net shape ceramic starting components which significantly reduce the amount of material that needs to be removed to complete the restoration.

In some embodiments, a fully sintered zirconia, fully crystallized lithium silicate or lithium disilicate, or other ceramic millable blank is provided with dimensions and shapes that are already close to the likely finished restoration. In some embodiments, this is accomplished by employing data regarding tooth sizes and shapes garnered over many previous patient experiences. As shown in FIGS. 2 to 5, by employing such data, it is possible to develop a rough composite shape 200, 300, 400, 500 for any type of tooth (i.e., upper or lower molar, incisor, bicuspid, anterior tooth, etc.) that reflects a large percentage of or all possible variations in size and shape from all such previous patient experiences. This rough composite can then be modified by a smoothing algorithm (see FIGS. 6 to 10) to provide a more practical configuration of a near net shape (NNS) milling blank 600, 700, 800, 900, 1000 in terms of handling and safety to avoid sharp points and narrow edges and reduce the surface complexity. This smoothing approach also makes it more practical from an initial fabrication standpoint by facilitating the use of injection molding techniques at a pre-sintered or partially sintered stage before the dentist receives the near net shape fully sintered components.

Figure 6A:
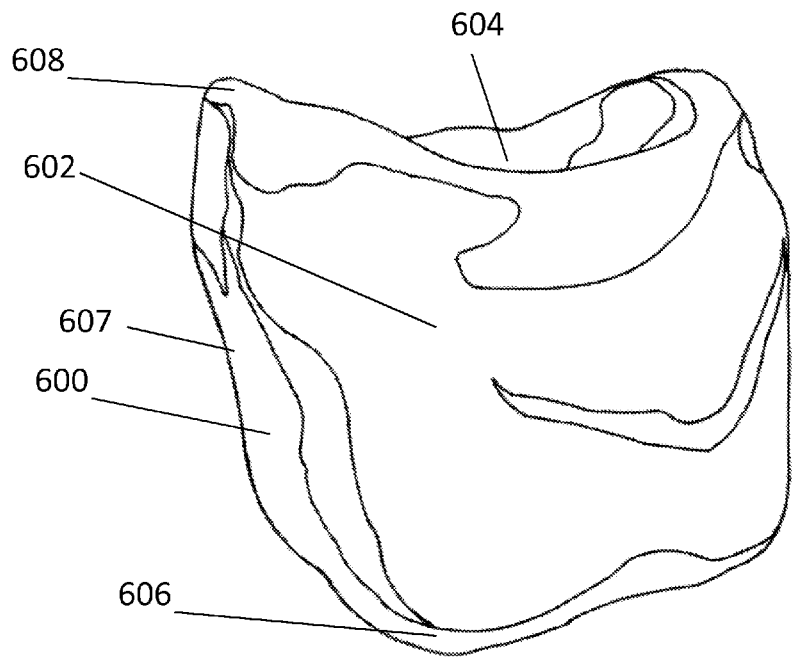
FIG. 6A is a drawing of a final shape molar corresponding to another step in the creation of an NNS millable blank.
Figure 6B:
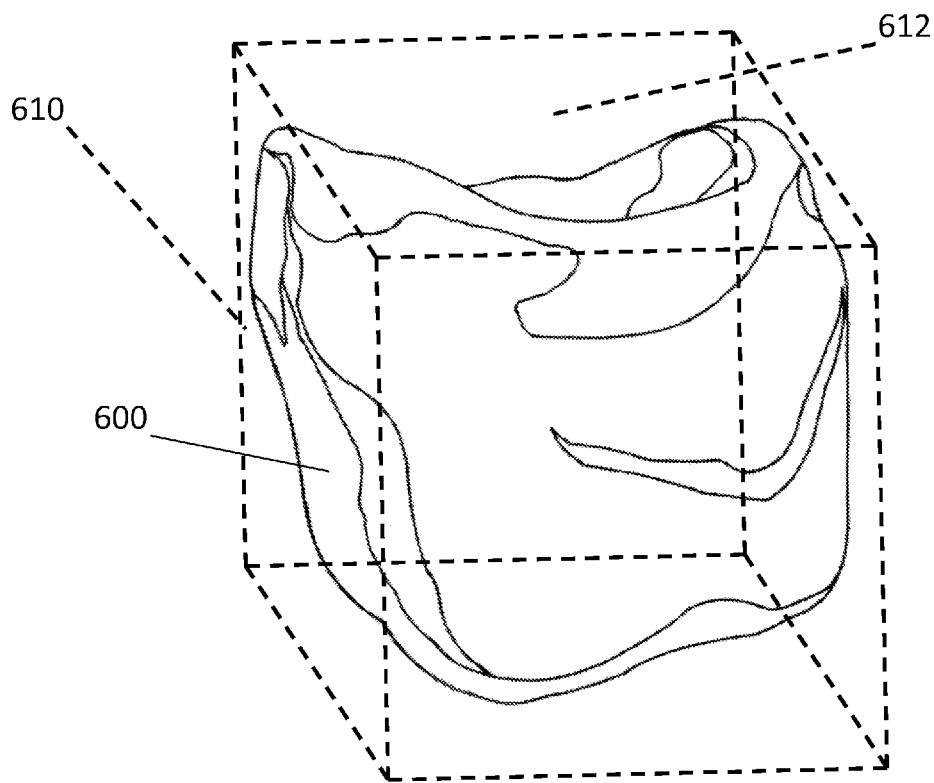
FIG. 6B is a drawing of the final shape molar of FIG. 6A, having superimposed thereon an imaginary bounding box.
Figure 7:
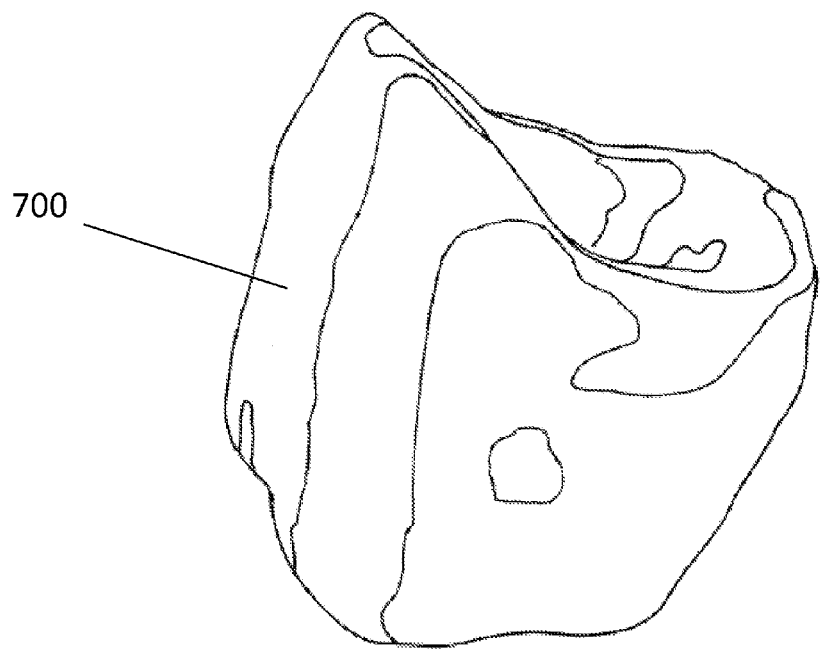
FIGS. 7 through 10 are additional drawings of a final shape molar corresponding to another step in the creation of an NNS millable blank.
Figure 8:
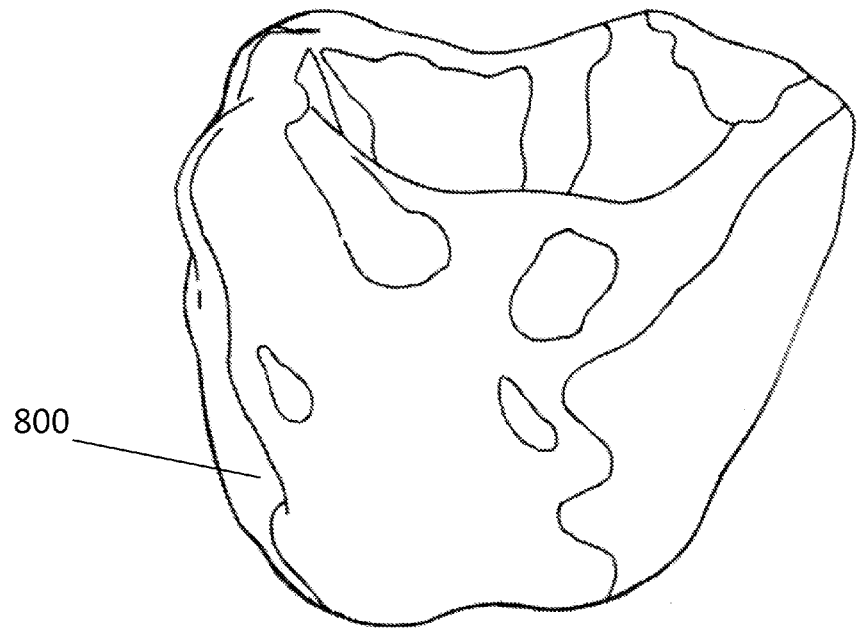
Figure 9:
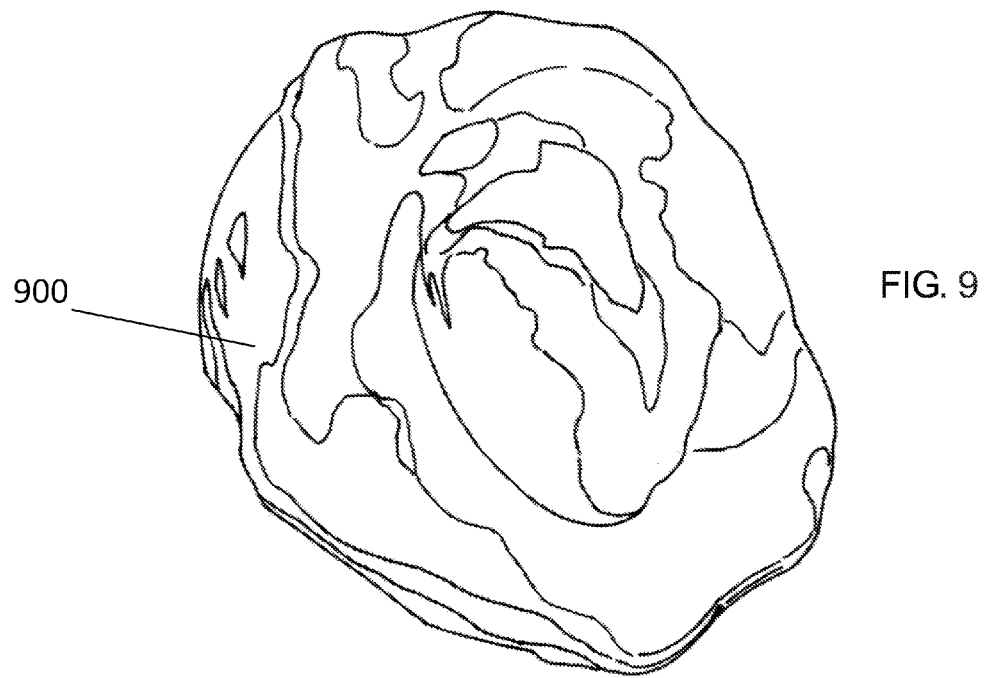
Figure 10:
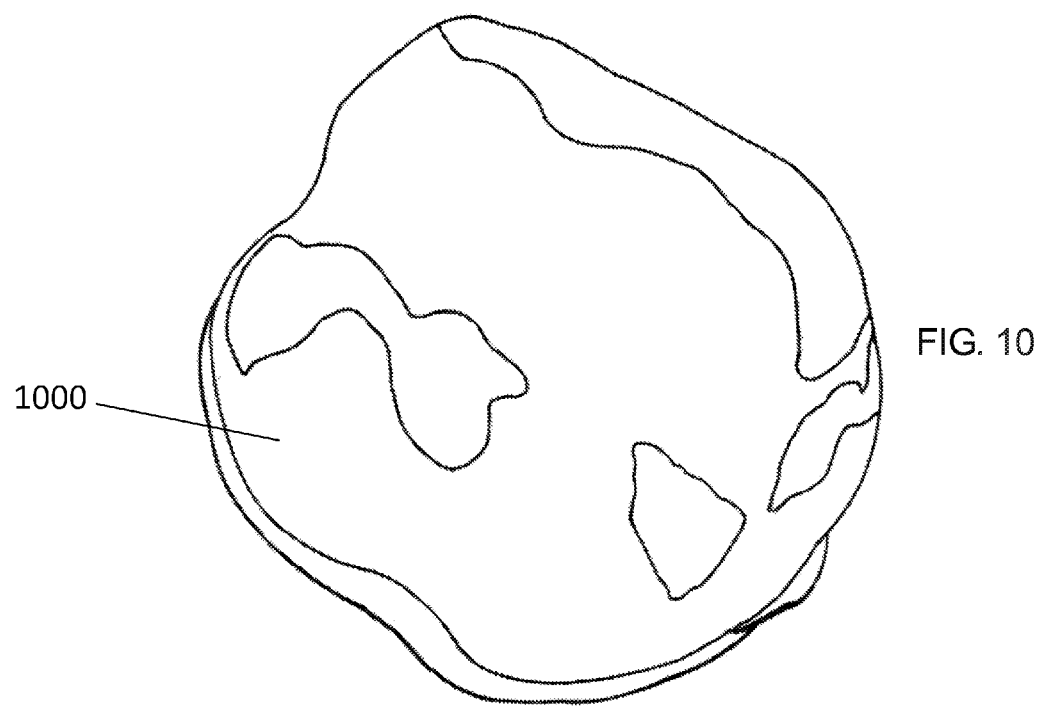

For example, and with reference to FIGS. 6A-B, an example of a near net shape millable blank 600 is shown.

The NNS millable blank 600 has an exterior surface 602 that is designed to accommodate a large percentage (e.g., 85%, 90%, 95%, or 98%) or all of a collection of prior patient restorations. The external surface 602 of the NNS millable blank 600 defines the volume of the millable blank 600. The external surface 602 also defines an internal void 604, an occlusal surface 606, side surfaces 607, and a margin area 608. Prior to machining, the internal void 604 of the millable blank 600 defines an internal void volume as described more fully below. After machining, the internal void 604 of the finished restoration will define a size and shape to accommodate the tooth preparation to which the restoration will be attached.

In the illustration shown in FIG. 6B, an imaginary bounding box 610 is provided. The bounding box 610 is a minimum-volume cube that contains the millable blank 600. The bounding box 610 is suitable for defining a cubic volume fraction for a given NNS millable blank, such as the millable blanks described herein and shown, e.g., in FIGS. 6A-B and 7-10. As used herein, the cubic volume fraction for an NNS millable blank is the volume of the NNS millable blank 600 divided by the volume of the imaginary bounding box 610. Accordingly, a cubic millable blank 600 having the dimensions of the bounding box 612 will provide a cubic volume fraction of 1.0, which constitutes a maximum value for the cubic volume fraction. Embodiments of the millable blanks 600 described herein may have a cubic volume fraction of from about 0.25 to about 1.0, such as from about 0.35 to about 0.95, such as from about 0.45 to about 0.90, such as from about 0.50 to about 0.85, such as from about 0.50 to about 0.80. Several examples of NNS millable blank cubic volume fractions are described in Table 1, below.

TABLE 1

NNS Millable Blank Cubic Volume Fraction Examples

| Example | Bounding Box Volume (mm³) | NNS Millable Blank Volume (mm³) | Cubic Volume Fraction of NNS Millable Blank |
|---|---|---|---|
| 1 (lower molar) | 1368.4 | 945.4 | 0.69 |
| 2 (lower molar) | 1811.9 | 1208.6 | 0.67 |
| 3 (lower molar) | 2290.2 | 1466.2 | 0.64 |
| 4 (premolar) | 915.8 | 662.1 | 0.72 |
| 5 (premolar) | 1081.5 | 682.2 | 0.63 |
| 6 (premolar) | 1930.1 | 1046.4 | 0.54 |
| 7 (upper molar) | 1652.9 | 1179.8 | 0.71 |
| 8 (upper molar) | 1838.6 | 1203.5 | 0.65 |

As noted above, and as shown in the embodiment illustrated in FIG. 6A, the NNS millable blank 600 includes an internal void 604 that may be considered as material removed (or not included) in a portion of the millable blank that will be shaped to accommodate the tooth preparation upon which the restoration will be attached. An internal void volume may be defined in relation to the imaginary bounding box 610 (see FIG. 6B) according to the following. First, the margin 608 of the millable blank is projected onto an upper surface 612 of the imaginary bounding box 610. Then, the volume of the internal void 604 is defined as the space that is both below the projection of the margin and above the surface of the millable blank defining the internal void 604. As used herein, the cubic volume fraction of the internal void for an NNS millable blank is the volume of the internal void 604 divided by the volume of the imaginary bounding box 610. Accordingly, a cubic millable blank 600 having the dimensions of the bounding box 612, or one having a flat surface opposite the occlusal surface 606, will provide an internal void cubic volume fraction of 0.0, which constitutes a minimum value for the internal void cubic volume fraction. Embodiments of the millable blanks 600 described herein may have an internal void cubic volume fraction of from about 0.0 to about 0.30, such as from about 0.05 to about 0.30, such as from about 0.05 to about 0.25, such as from about 0.05 to about 0.20, such as from about 0.05 to about 0.15.

In some embodiments, a ceramic mandrel is formed integrally with each of the near net shape millable blanks during the fabrication process. Current milling techniques require some way to affix the conventional ceramic block to the milling machine while permitting access to the block surfaces by the milling tool. This is normally accomplished by attaching a mandrel to the block. Such mandrels are usually made of metal, such as steel and are affixed by gluing the mandrel to the block to be at a known location and angle relative to the block surfaces. Unfortunately, such placement and gluing of the mandrel can be inaccurate. Such inaccuracy can be readily compensated for in a big block of ceramic material by controlling the milling process accordingly. However, in a near net shape component, such compensation would require a larger starting size and thus more material to be removed. That would at least partially defeat the advantage of using a near net shape component by increasing the resulting time for milling to achieve the final restoration. This disadvantage is overcome in some of the embodiments described herein by employing a mandrel 112 that is made of the same ceramic material as the millable blank 110 and integrating it into the near net shape component. (See FIG. 1C) Moreover, by employing such an integral ceramic mandrel, the current step of positioning, affixing and curing the mandrel/block interface is entirely obviated. Furthermore, by integrating a ceramic mandrel into the near net shape component, one can be far more accurate and consistent in mandrel location and angle and thus, for example, avoid the compensating enlargement of the near net shape component that would otherwise add to the amount of zirconia material that would need to be removed in a post-sintered milling process of a zirconia milling blank.

FIGS. 1A to 1E illustrate these unique and novel measures. More specifically, FIG. 1A shows the conventional block 100 before milling and FIG. 1B shows the conventional milled part 102 with affixed metal mandrel 104. FIG. 1C illustrates the near net shape component 110 with integral ceramic mandrel 112. FIG. 1D shows the NNS component 120 after final milling by the dentist. FIG. 1E shows the NNS component 130 prior to milling and without being attached to a mandrel.

Figure 12:
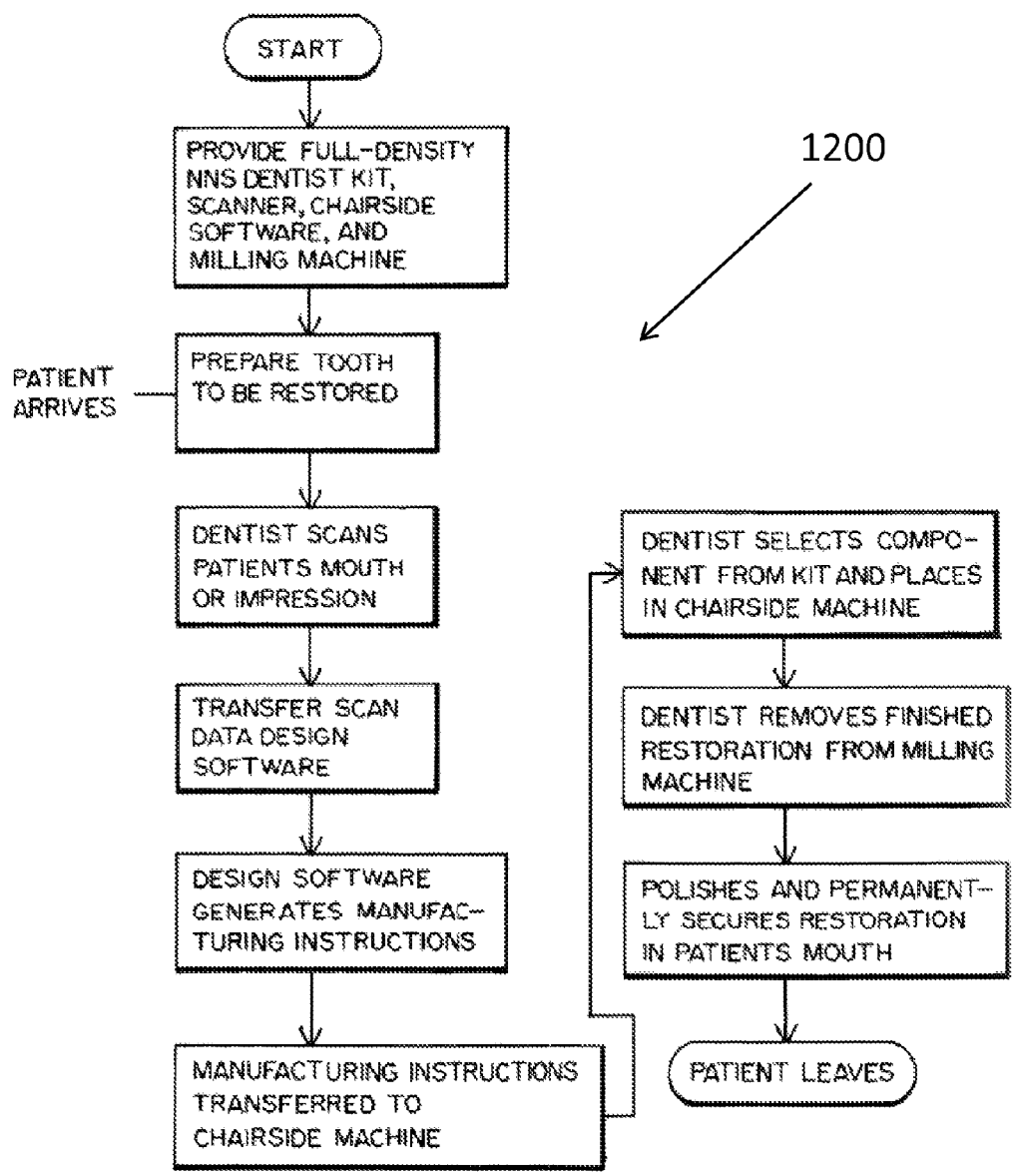
FIG. 12 is a flow chart drawing of a preferred ceramic restoration manufacturing process.

FIG. 12 illustrates, in flow chart format, the workflow 1200 for a dentist employing a near net shape (NNS) kit, a scanner and a chair-side milling machine to provide a patient with a dental restoration during one dental appointment. As indicated at the top of FIG. 12, the dentist will have been provided with the NNS component kit, scanner and chair-side milling machine with appropriate software. When the patient arrives, the tooth to be restored is prepared such as, for example, to receive a crown. Then the patient's mouth is scanned, or an impression is taken which can be scanned. Data from the scan is then transferred to design software for producing the restoration. This can be done locally, at a laboratory, or in the internet cloud through an automated design process depending on where the design software operation computer is located. If it is accomplished at a remote laboratory or in the internet cloud, the data is transferred over the internet.

Resulting manufacturing instructions are then transferred to the milling machine from the laboratory, internet cloud, or from the dentist's office equipment. At this point, the dentist selects the appropriate NNS millable blank from the NNS kit. In some embodiments, each kit will contain at least the minimum number of millable blanks needed to restore any tooth in the patient's mouth for both shape and shade. Shape is dictated by the nature of the tooth being restored. In some embodiments, there may be as few as one and as many as ten different shapes, such as, for example, between one and seven, or between two and six, depending on whether the tooth is an upper or lower tooth, a molar, a bicuspid, an incisor, an anterior tooth, etc. Shade is dictated by the precise color of adjacent teeth and, in some embodiments, is typically one of sixteen different shade selections which have been determined to encompass the vast majority of human tooth color variations. For example, in some embodiments, each NNS millable blank may be provided in up to sixteen different shade selections, such as up to ten different shade selections, such as up to seven different shade selections, such as up to four different shade selections. Thus, in some embodiments, a complete kit for restoring any likely tooth will contain from one up to about one hundred sixty NNS millable blanks, such as from one up to about seventy millable blanks, such as from one up to about sixteen millable blanks In some embodiments hereof, each such NNS millable blank will have an integral ceramic mandrel.

Figure 11:
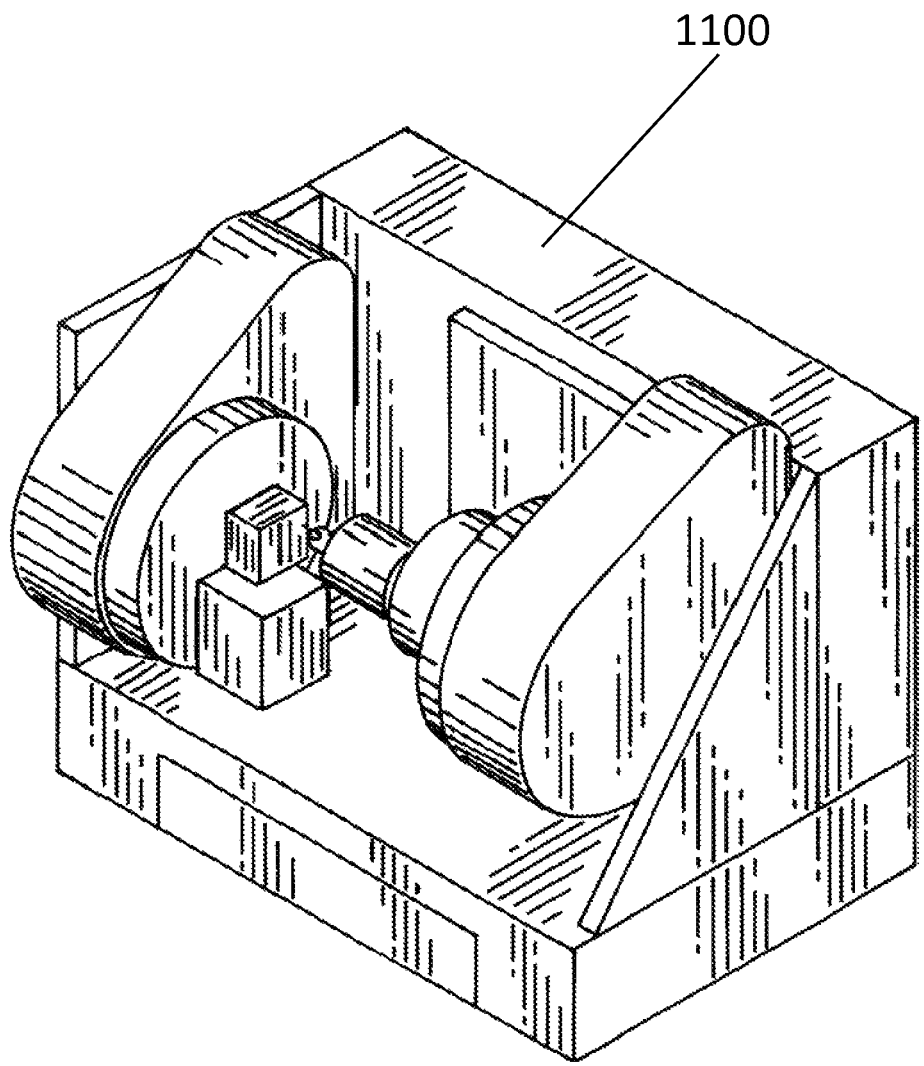
FIG. 11 is a drawing of a chair-side milling machine according to one embodiment hereof.

The dentist selects the appropriate NNS component and places it (employing the integral mandrel in those embodiments that include the integral mandrel) into the chair-side milling machine 1100. (See FIG. 11). After such installation, the milling machine follows the transferred manufacturing instructions to mill the component into a finished restoration needing only separation of the mandrel and polishing or brazing. As noted above, a suitable chair-side milling machine is disclosed in co-pending U.S. patent application Ser. No. 13/495,620 filed on Jun. 13, 2012, which is hereby incorporated by reference in its entirety. The details of the milling machine and its use are described therein, and will not be reproduced here. The dentist then installs the polished restoration and secures it in an otherwise conventional manner to complete the process.

It will now be understood that methods and apparatus described herein are suitable for preparing a fully contoured ceramic (e.g., zirconia, lithium silicate, lithium disilicate, or the like) restoration that may be fabricated and installed in a single patient appointment. Some of the described embodiments employ a kit comprising a plurality of near net shape, fully sintered zirconia and/or fully crystallized lithium silicate or lithium disilicate components having a minimal amount of excess material to be removed by a high speed milling machine in a matter of minutes. Each kit component may be based on a composite of a particular type of tooth derived from a plurality of patient data and smoothed to promote safe handling. A scanner generates patient data to facilitate the design of milling machine instructions and selection of the most conforming kit component of appropriate shape and shade.

We claim:

1. A near net shape (NNS) machinable block for fabricating a dental restoration, comprising:
   a machinable fully sintered zirconia ceramic material solid body having an external surface defining an occlusal surface area, a margin surface area, side surface areas between the occlusal surface area and the margin surface area, and an internal void surface area; and
   a mandrel attached to the solid body;
   wherein the external surface side surface areas consist essentially of non-planar surfaces;
   wherein the solid body is machinable into a monolithic ceramic dental restoration;
   wherein the solid body has a cubic volume fraction of between about 0.35 to about 0.95; and
   wherein the internal void surface area defines an internal void having an internal void volume.

2. The near net shape (NNS) machinable block of claim 1, wherein the solid body has a cubic volume fraction of between about 0.45 to about 0.90.

3. The near net shape (NNS) machinable block of claim 1, wherein the solid body has a cubic volume fraction of between about 0.50 to about 0.85.

4. The near net shape (NNS) machinable block of claim 1, wherein the solid body has a cubic volume fraction of between about 0.50 to about 0.80.

5. The near net shape (NNS) machinable block of claim 1, wherein the internal void volume has a cubic volume fraction of between about 0.05 to about 0.25.

6. The near net shape (NNS) machinable block of claim 1, wherein the internal void volume has a cubic volume fraction of between about 0.05 to about 0.20.

7. The near net shape (NNS) machinable block of claim 1, wherein the internal void volume has a cubic volume fraction of between about 0.05 to about 0.15.

8. The near net shape (NNS) machinable block of claim 1 wherein the mandrel is integrally formed with the solid body and comprises fully sintered zirconia.

9. A machinable block comprising:
   a machinable, fully crystallized or fully sintered zirconia ceramic material solid body having an external surface defining an occlusal surface area, a margin surface area, side surface areas between the occlusal surface area and the margin surface area, and an internal void surface area, wherein the external surface side surface areas consist essentially of non-planar surface areas; and
   a mandrel attached to the solid body;
   wherein the solid body is machinable into a fully contoured crown,
   wherein the solid body comprises a composite premolar body shape or a composite molar body shape and has a cubic volume fraction of between about 0.50 to about 0.80; and
   wherein the internal void surface area defines an internal void having an internal void volume, with the internal void volume having a cubic volume fraction of between about .05 and about 0.30.

10. The machinable block of claim 9, wherein the internal void volume has a cubic volume fraction of between about 0.05 to about 0.25.

11. The machinable block of claim 9, wherein the internal void volume has a cubic volume fraction of between about 0.05 to about 0.15.

12. The machinable block of claim 9, wherein the mandrel is integrally formed with the solid body, and the mandrel comprises fully sintered zirconia.

13. A kit comprising a plurality of dental components for fabricating dental restorations comprising:
   a plurality of sizes of machinable blocks, each block comprising:
      a machinable, fully sintered zirconia ceramic material solid body having an external surface defining an occlusal surface area, a margin surface area,
side surface areas between the occlusal surface area and the margin surface area, and an internal void surface area,
wherein the external surface side surface areas consist essentially of non-planar surface areas; and
wherein the solid body is machinable into a fully contoured crown; and
wherein the plurality of machinable blocks comprises more than one different shape to accommodate more than one different tooth type, and each machinable block solid body has a cubic volume fraction between about 0.50 to about 0.80.

14. The kit of claim 13 wherein the plurality of machinable blocks comprises a solid body having a composite premolar body shape.

15. The kit of claim 13 wherein the plurality of machinable blocks comprises a solid body having a composite molar body shape.

16. The kit of claim 13 wherein the plurality of machinable blocks comprises up to 10 different composite body shapes.

17. The kit of claim 13 wherein the plurality of machinable blocks comprises from 1 shade to 16 shade selections.

18. A kit for fabricating dental restorations comprising:
a plurality of machinable blocks, each machinable block comprising
a machinable, fully sintered zirconia ceramic material solid body having
an external surface defining an occlusal surface area, a margin surface area, side surface areas between the occlusal surface area and the margin surface area, and an internal void surface area,
wherein the external surface side surface areas consist essentially of non-planar side surface areas; and
wherein the machinable solid body has a cubic volume fraction of between about 0.35 to about 0.95 and is machinable into a zirconia ceramic dental restoration; and,
wherein the plurality of machinable blocks comprises a plurality of shade selections.

19. The kit of claim 18 wherein the plurality of machinable blocks comprises a plurality of different composite shapes to accommodate more than one tooth type.

20. The kit of 18, wherein the machinable block further comprises a sintered zirconia mandrel.

* * * * *